US009332897B2

(12) United States Patent
Watanabe

(10) Patent No.: US 9,332,897 B2
(45) Date of Patent: May 10, 2016

(54) FLUORESCENCE-IMAGING APPARATUS

(75) Inventor: Toshiaki Watanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 803 days.

(21) Appl. No.: 13/603,957

(22) Filed: Sep. 5, 2012

(65) Prior Publication Data

US 2012/0330165 A1    Dec. 27, 2012

Related U.S. Application Data

(63) Continuation of application No. PCT/JP2011/052316, filed on Feb. 4, 2011.

(30) Foreign Application Priority Data

Mar. 23, 2010    (JP) .................................. 2010-067020

(51) Int. Cl.
*A61B 6/00*    (2006.01)
*A61B 1/05*    (2006.01)
*A61B 1/00*    (2006.01)
*A61B 1/06*    (2006.01)
*A61B 1/04*    (2006.01)

(52) U.S. Cl.
CPC ............... *A61B 1/05* (2013.01); *A61B 1/00009* (2013.01); *A61B 1/043* (2013.01); *A61B 1/0646* (2013.01)

(58) Field of Classification Search
CPC ...... A61B 1/00009; A61B 1/043; A61B 1/05; A61B 1/0646
See application file for complete search history.

(56) References Cited

U.S. PATENT DOCUMENTS

2004/0208385 A1*    10/2004    Jiang ............................. 382/254
2009/0270702 A1*    10/2009    Zeng et al. ..................... 600/323
2010/0059690 A1*    3/2010    Ishihara ...................... 250/459.1

FOREIGN PATENT DOCUMENTS

| CN | 101583304 A | 11/2009 |
|----|-------------|---------|
| JP | 62-247232 A | 10/1987 |
| JP | 2001-258820 A | 9/2001 |
| JP | 2003-290130 A | 10/2003 |

OTHER PUBLICATIONS

International Search Report dated Mar. 1, 2011 issued in PCT/JP2011/052316.

* cited by examiner

*Primary Examiner* — James Kish
*Assistant Examiner* — Saurel J Selkin
(74) *Attorney, Agent, or Firm* — Scully, Scott, Murphy & Presser, P.C.

(57) ABSTRACT

A fluoroscopy apparatus is adopted which includes a fluorescence-image generating section that generates a fluorescence image of a subject, a white-light-image generating section that generates a white-light image of the subject, a fluorescence-image correcting section that generates a corrected fluorescence image in which luminance values of pixels are normalized by dividing the luminance values of the pixels of the fluorescence image by the luminance values of the pixels of the white-light image, an error-image identifying section that standardizes white-light-image acquisition conditions and identifies an error region, which is a region in which the luminance values of the corrected fluorescence image exceed a preset allowable error range, on the basis of a gray level of the normalized white-light image, and a monitor that displays the error region.

10 Claims, 14 Drawing Sheets

FLUORESCENCE-IMAGING APPARATUS

CROSS-REFERENCE TO RELATED APPLICATIONS

This is a continuation of International Application PCT/JP2011/052316, with an international filing date of Feb. 4, 2011, which is hereby incorporated by reference herein in its entirety. This application is based on Japanese Patent Application No. 2010-067020, the contents of which are incorporated herein by reference.

TECHNICAL FIELD

The present invention relates to a fluoroscopy apparatus.

BACKGROUND ART

In fluoroscopy apparatuses that diagnose a lesion region using a fluorescent agent, a known method in the related art divides the luminance values of the individual pixels of a fluorescence image by the luminance values of the individual pixels of a reference-light image to correct the fluorescence image because the intensity of irradiated light changes depending on the observation distance (for example, see PTL 1).

CITATION LIST

Patent Literature

{PTL 1} Japanese Unexamined Patent Application, Publication No. SHO 62-247232

SUMMARY OF INVENTION

The present invention adopts a fluoroscopy apparatus including a light source unit that generates illumination light and excitation light to be radiated onto a subject; a fluorescence-image generating section that generates a fluorescence image by image-capturing fluorescence generated in the subject by irradiation with the excitation light from the light source unit; a return-light-image generating section that generates a return-light image by image-capturing return light that returns from the subject by irradiation with the illumination light from the light source unit; a fluorescence-image correcting section that generates a corrected fluorescence image in which luminance values of pixels are normalized by dividing the luminance values of the pixels of the fluorescence image generated by the fluorescence-image generating section by the luminance values of the pixels of the return-light image generated by the return-light-image generating section; an error-image identifying section that standardizes image-acquisition conditions for the return-light image generated by the return-light-image generating section and identifies an error region, which is a region in which the luminance values of the corrected fluorescence image exceed a preset allowable error range, on the basis of a gray level of the normalized return-light image; and an image display unit that displays the error region identified by the error-image identifying section.

DESCRIPTION OF EMBODIMENTS

First Embodiment

A fluoroscopy apparatus 1 according to a first embodiment of the present invention will be described hereinbelow with reference to the drawings. Here, an example in which the fluoroscopy apparatus 1 according to this embodiment is applied to an endoscope apparatus will be described.

Figure 1:
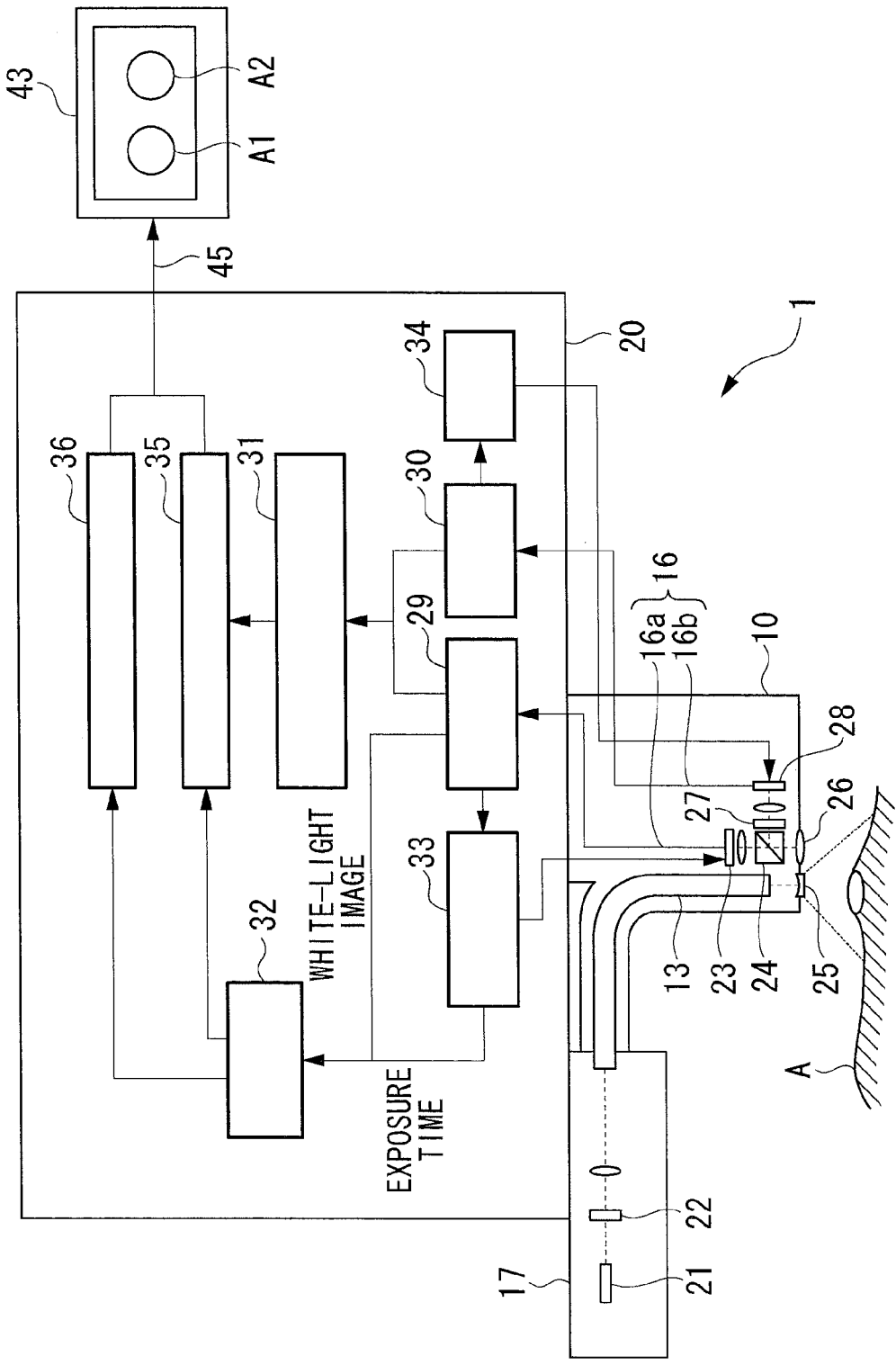
FIG. 1 is a functional block diagram of a fluoroscopy apparatus according to a first embodiment of the present invention.

As shown in FIG. 1, the fluoroscopy apparatus 1 is equipped with an endoscope 10, a light source device (light source unit) 17, an image computing unit 20, and a monitor (image display unit) 43.

The endoscope 10 has an elongated inserted portion to be inserted into a body cavity, in which a light guide fiber 13 is provided. One end of the light guide fiber 13 extends to the distal end of the endoscope 10, and the other end is connected to the light source device 17. This allows light emitted from the light source device 17 to be guided to the distal end of the endoscope 10 to irradiate a subject A in the body cavity.

The endoscope 10 and the image computing unit 20 are connected by an image transmission cable 16. The image computing unit 20 and the monitor 43 are connected by a monitor cable 45. This allows image data obtained by the endoscope 10 to be sent to the image computing unit 20 through the image transmission cable 16. The sent image data is subjected to image processing in the image computing unit 20, is then transmitted to the monitor 43 through the monitor cable 45, and is displayed on a monitor screen.

Next, the detailed configuration of the fluoroscopy apparatus 1 of this embodiment and a display on the monitor screen will be described.

Figure 2:
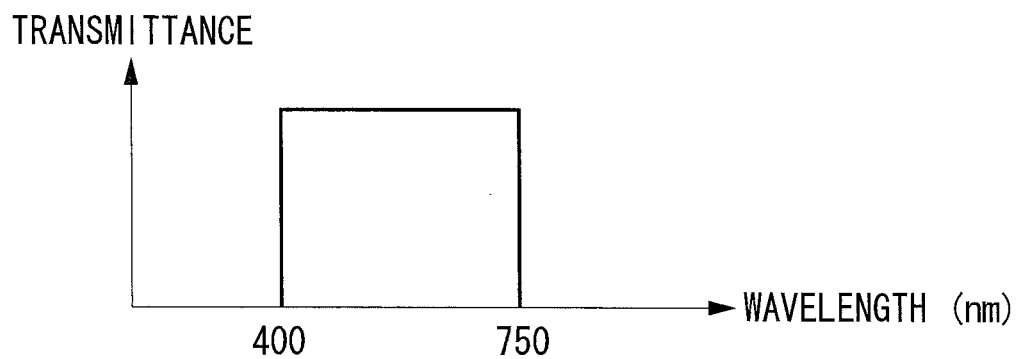
FIG. 2 is a graph showing the transmittance characteristics of an excitation-light transmitting filter in FIG. 1.

As shown in FIG. 1, the light source device 17 accommodates a xenon lamp (Xe lamp) 21 and a wavelength selection filter 22. The Xe lamp 21 generates white light and excitation light. The light generated from the Xe lamp 21 passes through the wavelength selection filter 22, and thus, white light and excitation light only in a set wavelength band pass therethrough. Specifically, as shown in FIG. 2, the wavelength selection filter 22 allows light in a wavelength band of 400 nm to 750 nm to pass through and reflects light in the other wavelength bands.

As shown in FIG. 1, the endoscope 10 accommodates the light guide fiber 13, a white-light color CCD 23, a splitter 24, an illumination optical system 25, an image acquisition optical system 26, an excitation-light cut filter 27, and a fluorescence monochrome CCD 28.

The white light and excitation light emitted from the light source device 17 are guided by the light guide fiber 13 in the endoscope 10 and are radiated onto the subject A by the illumination optical system 25 disposed at the distal end of the endoscope 10. By irradiating the subject A with the white light, reflected light coming from the subject A enters the image acquisition optical system 26 disposed at the distal end of the endoscope 10. By irradiating the subject A with the excitation light, fluorescence is generated in the subject A, and the fluorescence enters the image acquisition optical system 26.

The splitter 24 allows the reflected light coming from the subject A to pass through and reflects the fluorescence generated in the subject A. Because of such characteristics, the splitter 24 separates the reflected light and the fluorescence that enter the image acquisition optical system 26 from each other. Since the wavelength of the fluorescence at that time is shifted to the long wavelength side relative to the wavelength of the excitation light, a splitter that reflects light closer to the long wavelength side than the wavelength of the excitation light is used.

Figure 3:
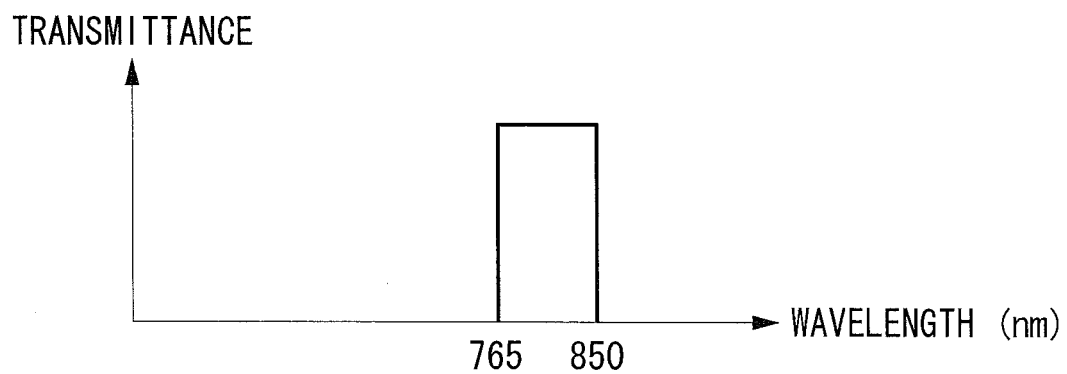
FIG. 3 is a graph showing the transmittance characteristics of an excitation-light cut filter in FIG. 1.

The excitation-light cut filter 27 is a filter for removing the excitation light (reflected light) from the fluorescence. Specifically, as shown in FIG. 3, the splitter 24 allows light in a wavelength band of 765 nm to 850 nm to pass through and reflects light in the other wavelength bands.

The fluorescence is completely separated from the excitation light (reflected light) by passing through the excitation-light cut filter 27, and the separated fluorescence is detected by the fluorescence monochrome CCD 28. Since the separated fluorescence is weak, the fluorescence monochrome CCD 28 used has higher sensitivity than the white-light color CCD 23. Fluorescence image data detected by the fluorescence monochrome CCD 28 is sent to a fluorescence-image generating section 30 in the image computing unit 20 through an image transmission cable 16*b*.

On the other hand, the reflected light coming from the subject A, which has passed through the splitter 24, is detected by the white-light color CCD 23. The white-light image data detected by the white-light color CCD 23 is sent to a white-light-image generating section 29 in the image computing unit 20 through an image transmission cable 16*a*.

As shown in FIG. 1, the image computing unit 20 includes, as the functions thereof, the white-light-image generating section (return-light-image generating section) 29, the fluorescence-image generating section 30, a fluorescence-image correcting section 31, an error-image identifying section 32, an automatic exposure-time adjusting section 33, an automatic gain control (AGC) 34, a post-processing section 35, and an error display section 36.

The white-light-image generating section 29 generates a white-light image from the white-light image data detected by the white-light color CCD 23. The white-light-image generating section 29 transmits the generated white-light image to the fluorescence-image correcting section 31, the error-image identifying section 32, and the automatic exposure-time adjusting section 33.

The fluorescence-image generating section 30 generates a fluorescence image from the fluorescence image data detected by the fluorescence monochrome CCD 28. The fluorescence-image generating section 30 transmits the generated fluorescence image to the fluorescence-image correcting section 31 and the AGC 34.

The fluorescence-image correcting section 31 generates a corrected fluorescence image in which the luminance values of the pixels are normalized by dividing the luminance values of the pixels of the fluorescence image generated by the fluorescence-image generating section 30 by the luminance values of the pixels of the white-light image generated by the white-light-image generating section 29, corresponding to the pixels of the fluorescence image. The fluorescence-image correcting section 31 transmits the generated corrected fluorescence image to the post-processing section 35.

The automatic exposure-time adjusting section 33 adjusts the exposure time of the white-light color CCD 23 on the basis of the luminance values of the white-light image generated by the white-light-image generating section 29.

The AGC 34 adjusts the gain of the fluorescence monochrome CCD 28 on the basis of the luminance values of the fluorescence image generated by the fluorescence-image generating section 30.

The error-image identifying section 32 standardizes the image-acquisition conditions for the white-light image generated by the white-light-image generating section 29 and identifies an error region on the basis of a gray level of the normalized white-light image. Here, examples of the image-acquisition conditions for the white-light image are the exposure time and gain of the white-light color CCD 23 and the intensity of illumination light emitted from the light source unit.

Specifically, the error-image identifying section 32 standardizes the image-acquisition conditions for the white-light image by dividing the luminance values of the pixels of the white-light image generated by the white-light-image generating section 29 by the exposure time of the white-light color CCD 23 adjusted by the automatic exposure-time adjusting section 33. The error-image identifying section 32 converts the gray level of the normalized white-light image to an observation distance and identifies a region in which this observation distance is smaller than a preset threshold value as an error region. Here, the error region is a region in which the luminance values of the corrected fluorescence image exceed a preset allowable error range.

Furthermore, if the area of a region at a high gray level in the normalized white-light image is larger than a preset area (for example, 1,000 pixels), the error-image identifying section 32 identifies this region as an error region.

Here, the region at a high gray level in the normalized white-light image also includes a specular-reflection region in which the intensity of the white light is high because the illumination light is specularly reflected. Thus, identifying an error region by using the area of the region at a high gray level, as described above, allows identification of an error region that excludes the specular-reflection region, thus improving the error-region identification accuracy.

The post-processing section 35 combines the white-light image generated by the white-light-image generating section 29, the corrected fluorescence image generated by the fluorescence-image correcting section 31, and the error region identified by the error-image identifying section 32 to generate a combined image. Specifically, the post-processing section 35 classifies the lesion level depending on the gray level of the corrected fluorescence image generated by the fluorescence-image correcting section 31. Then, the post-processing section 35 superimposes a region at a predetermined level or higher on the data of the white-light image to display a lesion site.

Figure 4:
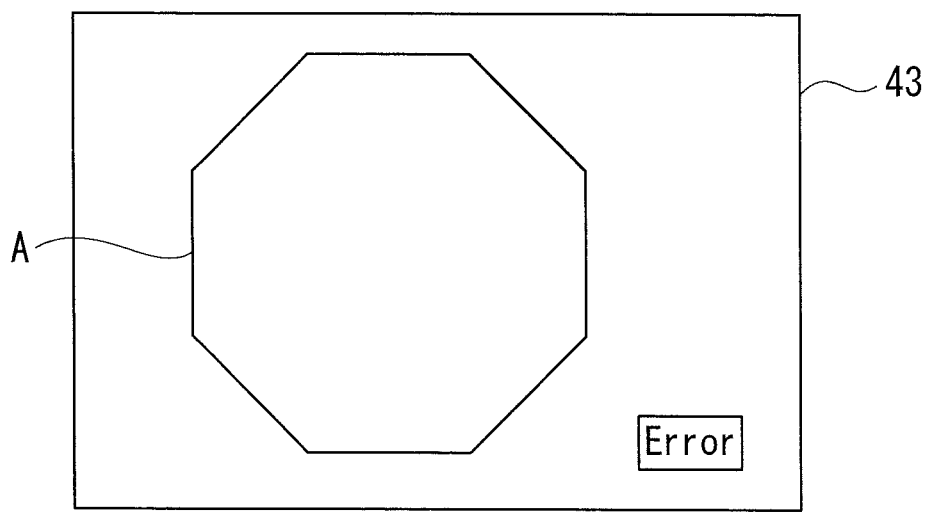
FIG. 4 is a diagram of an example of a screen displayed on the monitor in FIG. 1.

If it is determined by the error-image identifying section 32 that an error region is present, the error display section 36 displays an error indication on the screen of the monitor 43, as shown in FIG. 4. The error indication includes not only displaying the word "Error", as shown in FIG. 4, but also flashing the word and displaying the word in color.

The error indication on the screen allows the operator to recognize that an error region is present, that is, that the observation distance is too short, and prompts the operator to perform reobservation in the error region, so that overlooking and so on of a lesion region can be prevented.

The monitor 43 displays the image generated by the post-processing section 35 and the error display image generated by the error display section 36 on the screen.

The monitor 43 may be configured to allow the user to set, among a plurality of observation modes, an observation mode in which an image is to be displayed on the monitor 43 by using an observation-mode switching section (not shown). Here, examples of the plurality of observation modes include an observation mode in which a white-light image A1 generated by the white-light-image generating section 29 is displayed directly on the monitor 43 (white-light-image observation mode), an observation mode in which a combined image A2 generated by the post-processing section 35 is displayed on the monitor 43 (combined-image observation mode), and an observation mode in which the white-light image A1 and the combined image A2 are displayed at the same time (two-image observation mode).

The operation of the fluoroscopy apparatus 1 having the above configuration will be described hereinbelow.

First, when the fluoroscopy apparatus 1 of this embodiment is used to start observation of the subject A, light from the light source device 17 irradiates the subject A via the light guide fiber 13. Thus, a white-light image generated by the white-light-image generating section 29 from the reflected light coming from the subject A is acquired, and a fluorescence image generated by the fluorescence-image generating section 30 from fluorescence emitted from the subject A is acquired.

Next, a corrected fluorescence image is generated by the fluorescence-image correcting section 31 by dividing the luminance values of the pixels of the fluorescence image by the luminance values of the pixels of the white-light image.

At that time, the exposure time of the white-light color CCD 23 is adjusted by the automatic exposure-time adjusting section 33, and the gain of the fluorescence monochrome CCD 28 is adjusted by the AGC 34.

Identification of the error region is performed by the error-image identifying section 32. The details of this process will be described later.

Next, the corrected fluorescence image and the white-light image are combined by the post-processing section 35. If an error region is identified by the error-image identifying section 32, an error display image is generated by the error display section 36.

The thus-generated combined image and error display image are displayed on the monitor 43, in accordance with the set observation mode.

Figure 5:
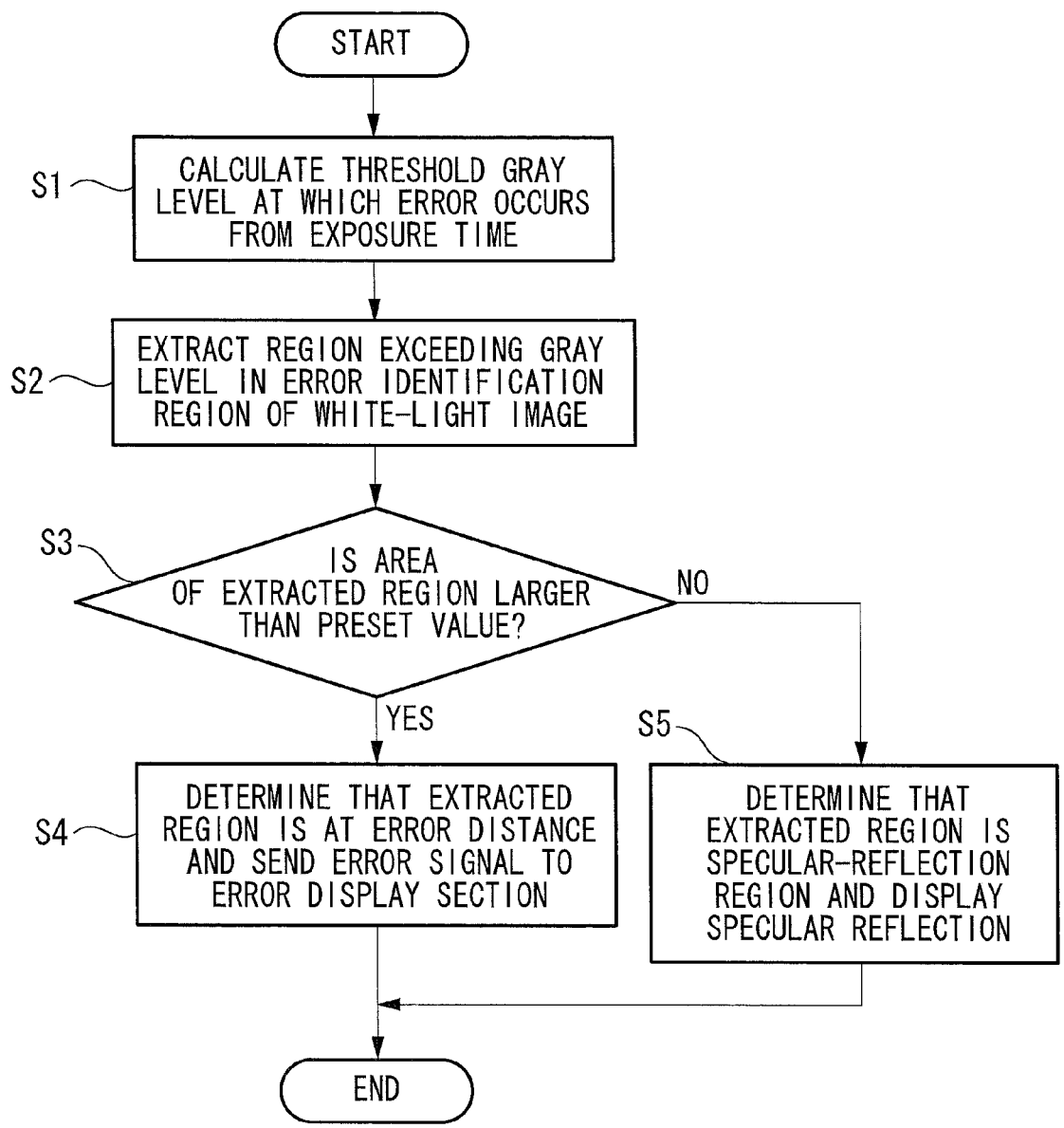
FIG. 5 is a flowchart explaining a process for displaying an error region.

A method for identifying an error region performed by the error-image identifying section 32 will be described below using a flowchart shown in FIG. 5.

An observation distance for error identification, that is, a gray level of the normalized white-light image, which is obtained by dividing the gray level of the white-light image by the exposure time of the white-light color CCD 23, is set in advance as a precondition.

First, a gray level (threshold gray level) of the normalized white-light image for error identification is calculated from the exposure time of the white-light color CCD 23 (step S1).

Next, a region of the normalized white-light image having gray levels exceeding the above-described threshold gray level is extracted (step S2).

Next, it is determined whether or not the area of the thus-extracted region is larger than a preset area (for example, 1,000 pixels) (step S3).

If it is determined in step S3 that the area of the extracted region is larger than the preset area, it is determined that the region is at the error distance, that is, that the observation distance is too short, and a signal for displaying an error is transmitted to the error display section 36 (step S4).

In contrast, if it is determined in step S3 that the area of the extracted region is smaller than the preset area, it is determined that the extracted region is a specular-reflection region, and the combined image is displayed directly on the monitor 43 (step S5).

As described above, with the fluoroscopy apparatus 1 according to this embodiment, by generating a corrected fluorescence image in which the luminance values of the pixels are normalized by dividing the luminance values of the pixels of the fluorescence image by the luminance values of the pixels of the white-light image, and by displaying the state of the subject A on the basis of the corrected fluorescence image, the state of the subject A can be determined while eliminating the influence of the observation distance and the observation angle on the intensity of the fluorescence, so that the lesion-region observation accuracy can be improved.

If the observation distance is short, a large error occurs in the result of division using the white-light image, that is, the luminance values of the corrected fluorescence image, depending on whether the white light in the illumination light and the fluorescence are scattered at the surface or inside. In this case, standardizing the image-acquisition conditions for the white-light image to identify an error region using the error-image identifying section 32 allows a region in which the luminance values of the corrected fluorescence image exceed a preset allowable error range, that is, a region in which improper correction is performed, to be displayed as an error region, even if the observation distance is short, so that overlooking and so on of a lesion region can be prevented.

Furthermore, displaying the error region identified by the error-image identifying section 32 on the monitor 43 so as to be superimposed on the white-light image generated by the white-light-image generating section 29 allows the operator to recognize the position of the error region of the subject A in the white-light image, which prompts the operator to perform reobservation in the error region, so that overlooking and so on of a lesion region can be prevented.

Figure 6A:
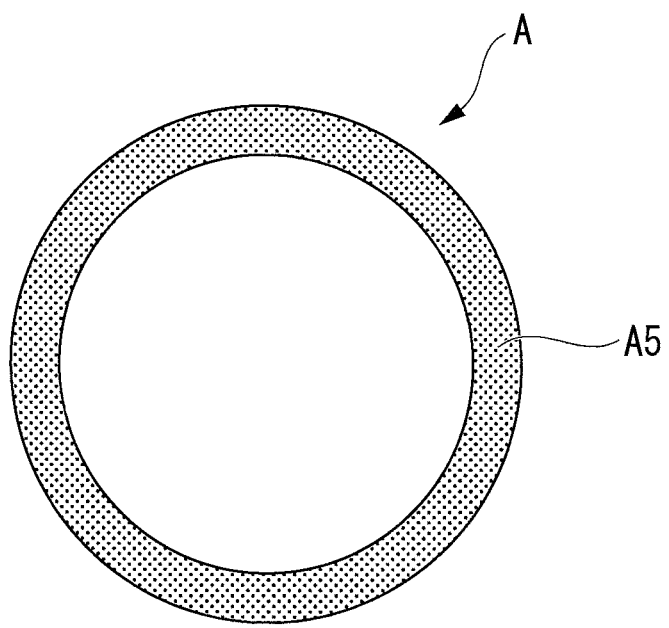
FIG. 6A is a diagram explaining an error detection region, showing an example of a circular image.
Figure 6B:
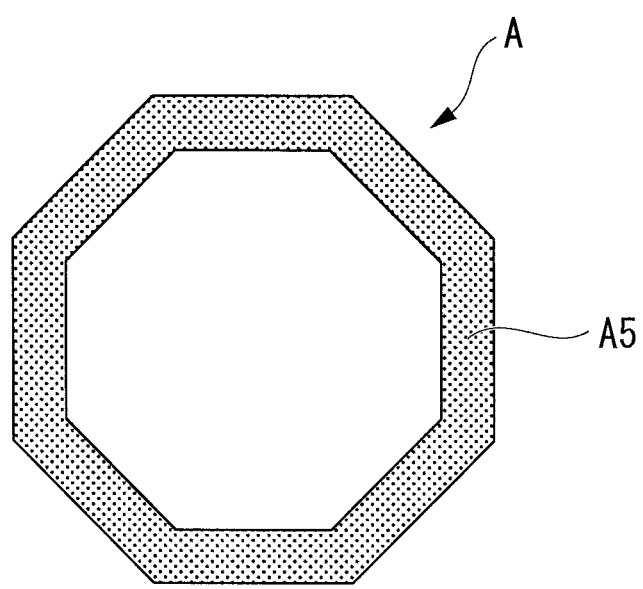
FIG. 6B is a diagram explaining an error detection region, showing an example of an octagonal image.

In the fluoroscopy apparatus 1 according to this embodiment, as shown in FIGS. 6A and 6B, the error-image identifying section 32 may identify an error region on the basis of a gray level of a peripheral region A5 of the normalized white-light image.

Because the peripheral region A5 of the image tends to become brighter due to reflected light or the like coming from the inner wall of the body cavity, identification of an error region based on a gray level of this peripheral region A5 can reduce the amount of calculation when identifying the error region, thus allowing high-speed processing.

Figure 7A:
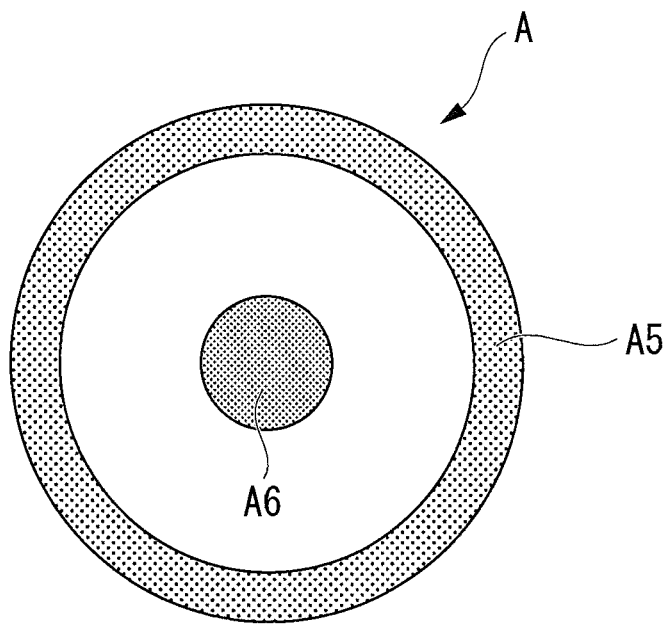
FIG. 7A is a diagram explaining an error detection region, showing an example of a circular image.
Figure 7B:
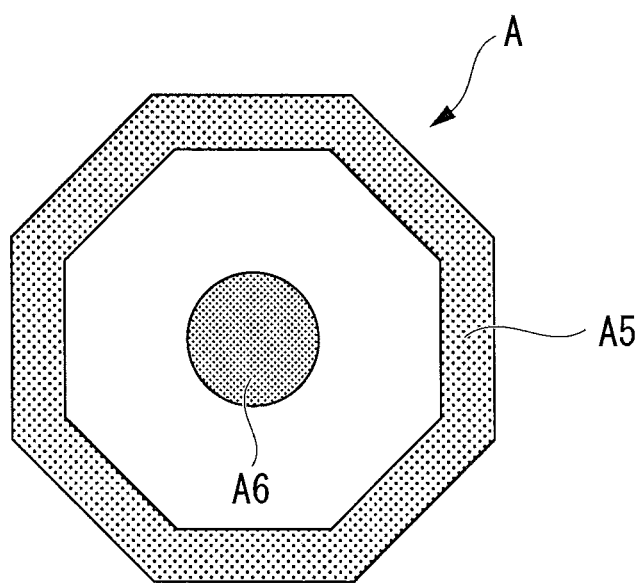
FIG. 7B is a diagram explaining an error detection region, showing an example of an octagonal image.

As shown in FIGS. 7A and 7B, the error-image identifying section 32 may identify an error region on the basis of gray levels of the peripheral region A5 and a central region A6 of the normalized white-light image.

The peripheral region A5 of the image tends to become brighter due to reflected light and so on coming from the inner wall of the body cavity, and the central region A6 of the image tends to become brighter due to the short distance from an illumination-light emitting portion. Accordingly, identification of an error region based on gray levels of the peripheral region A5 and the central region A6 of the image can reduce the amount of calculation when identifying the error region, thus allowing high-speed processing.

Figure 8A:
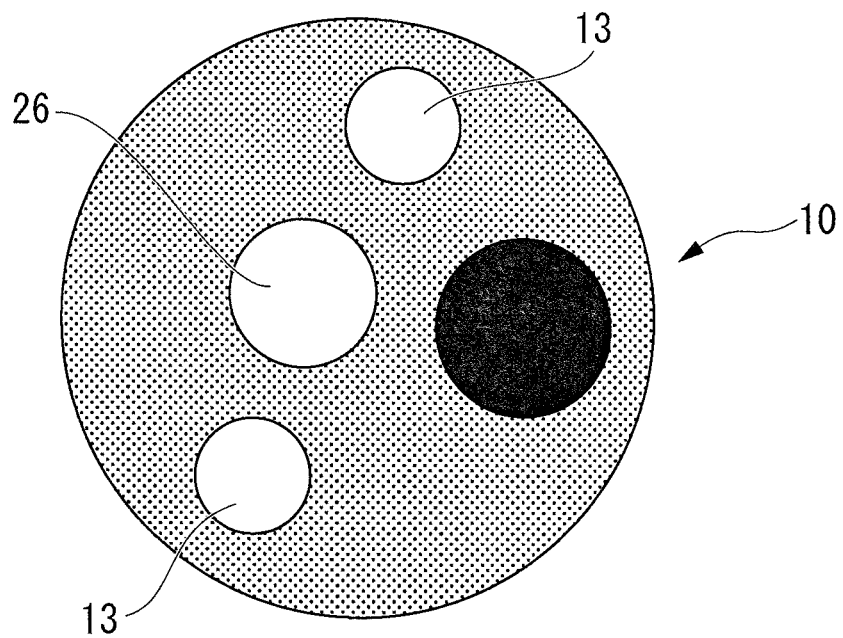
FIG. 8A is a diagram explaining an error detection region, showing a plan view of the distal end of an endoscope.
Figure 8B:
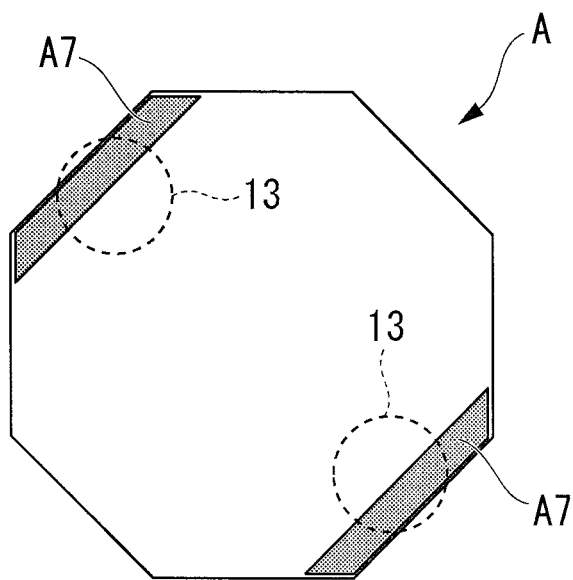
FIG. 8B is a diagram explaining error detection regions corresponding to the endoscope in FIG. 8A.

As shown in FIGS. 8A and 8B, the error-image identifying section 32 may identify an error region on the basis of gray levels of regions A7 in the normalized white-light image corresponding to the vicinity of the illumination-light emitting end (the distal end of the light guide fiber 13). Here, FIG. 8A shows a plan view of the distal end face of the endoscope 10, and FIG. 8B shows an image of the subject A.

Since the vicinity of the illumination-light emitting end tends to become brighter, identification of an error region based on gray levels of the regions A7 of the white-light image corresponding to the vicinity of the illumination-light emitting end can reduce the amount of calculation when identifying the error region, thus allowing high-speed processing.

Second Embodiment

Next, a fluoroscopy apparatus 2 according to a second embodiment of the present invention will be described with reference to the drawings. In the description of this embodiment, descriptions of commonalities with the fluoroscopy apparatus 1 according to the first embodiment will be omitted, and the difference will be mainly described.

The difference between the fluoroscopy apparatus 2 according to this embodiment and the fluoroscopy apparatus 1 according to the first embodiment is that the error region is displayed in color.

Figure 9:
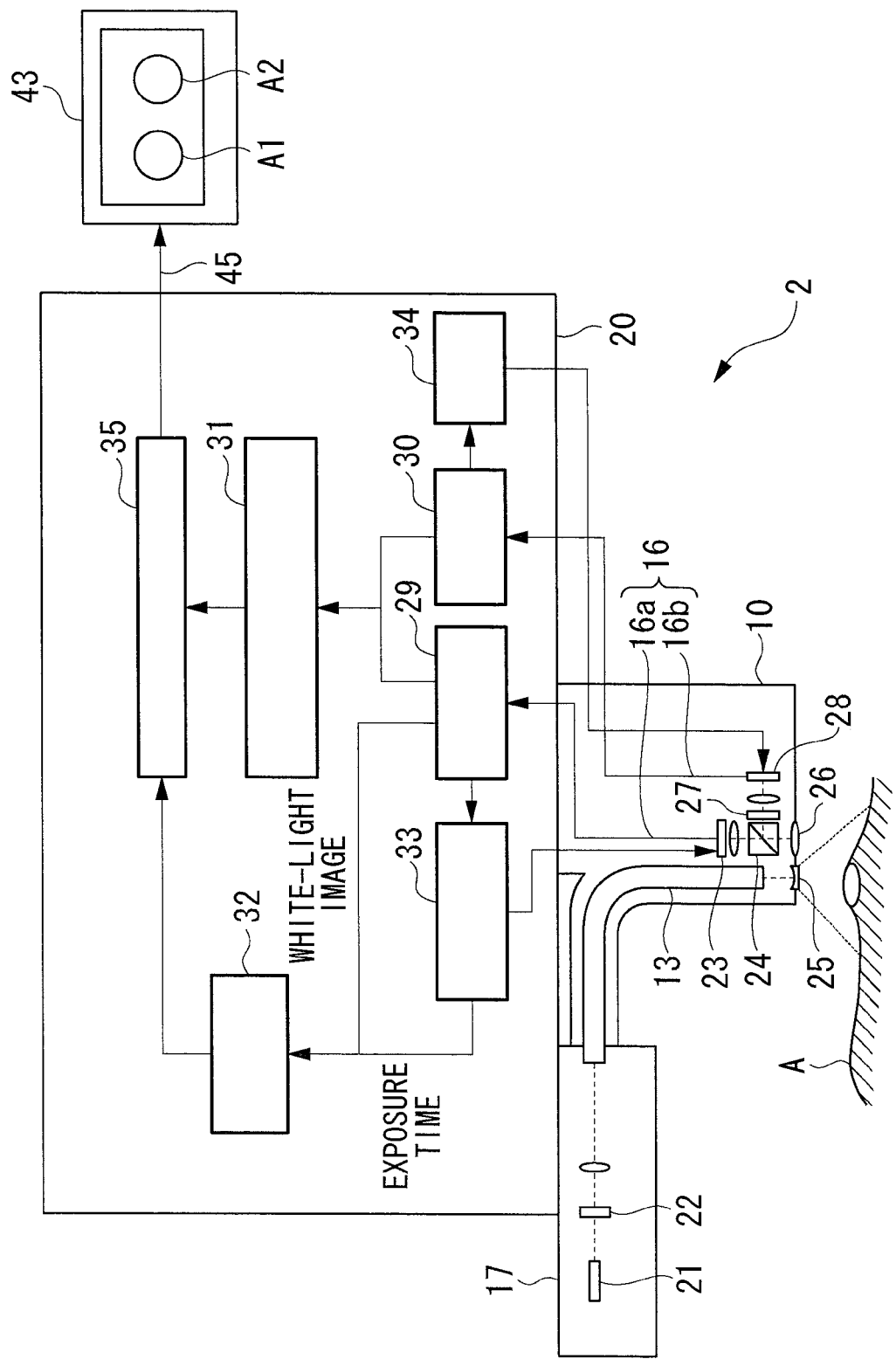
FIG. 9 is a functional block diagram of a fluoroscopy apparatus according to a second embodiment of the present invention.

As shown in FIG. 9, in the fluoroscopy apparatus 2 according to this embodiment, the image computing unit 20 includes, as the functions thereof, the white-light-image generating section (return-light-image generating section) 29, the fluorescence-image generating section 30, the fluorescence-image correcting section 31, the error-image identifying section 32, the automatic exposure-time adjusting section 33, the automatic gain control (AGC) 34, and the post-processing section (state determination section) 35.

The post-processing section 35 combines the white-light image generated by the white-light-image generating section 29, the corrected fluorescence image generated by the fluorescence-image correcting section 31, and the error region identified by the error-image identifying section 32 to generate a combined image. Specifically, the post-processing section 35 classifies the lesion level depending on the gray level of the corrected fluorescence image generated by the fluorescence-image correcting section 31 and displays the individual lesion levels in pseudo-color. The error region identified by the error-image identifying section 32 is represented in a color different from that of regions other than the error region (for example, gray or yellow).

Figure 10:
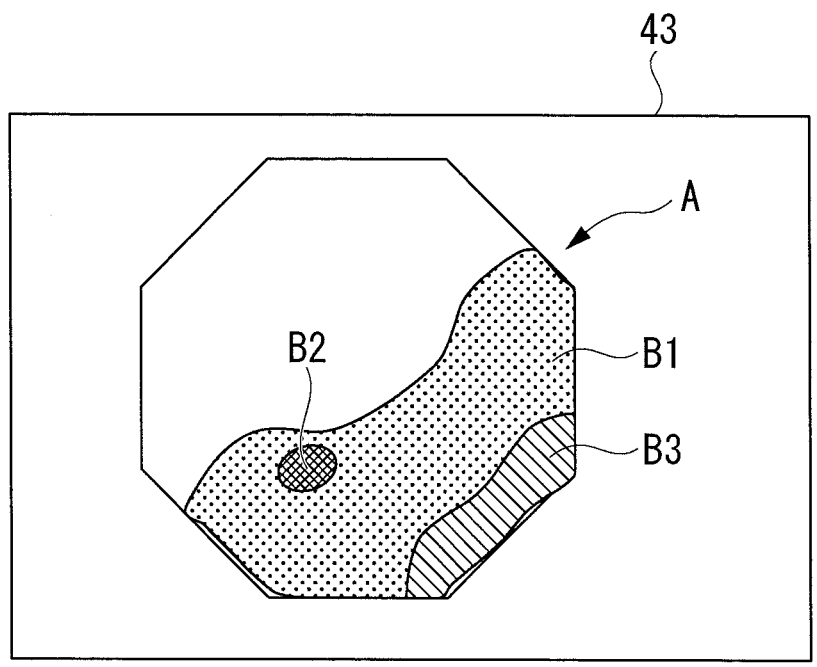
FIG. 10 is a diagram of an example of a screen displayed on the monitor of the fluoroscopy apparatus in FIG. 9.

By combining the pseudo-colored and colored images in this way, the subject A can be displayed, on the monitor 43, in different colors classified into a normal region B1, a lesion region B2, and an error region B3, as shown in FIG. 10.

Displaying the error region B3 in a different color, as described above, allows the error region B3 in the white-light image of the subject A to be displayed so that the operator can easily recognize the position of the error region B3 and prompts the operator to perform reobservation in the error region B3, so that overlooking and so on of the lesion region B2 can be prevented.

Third Embodiment

Next, a fluoroscopy apparatus 3 according to a third embodiment of the present invention will be described with reference to the drawings. In the description of this embodiment, descriptions of commonalities with the fluoroscopy apparatus 1 according to the first embodiment will be omitted, and the difference will be mainly described.

The difference between the fluoroscopy apparatus 3 according to this embodiment and the fluoroscopy apparatus 1 according to the first embodiment is that an error identification condition is set for each scope (endoscope) mounted thereon.

Figure 11:
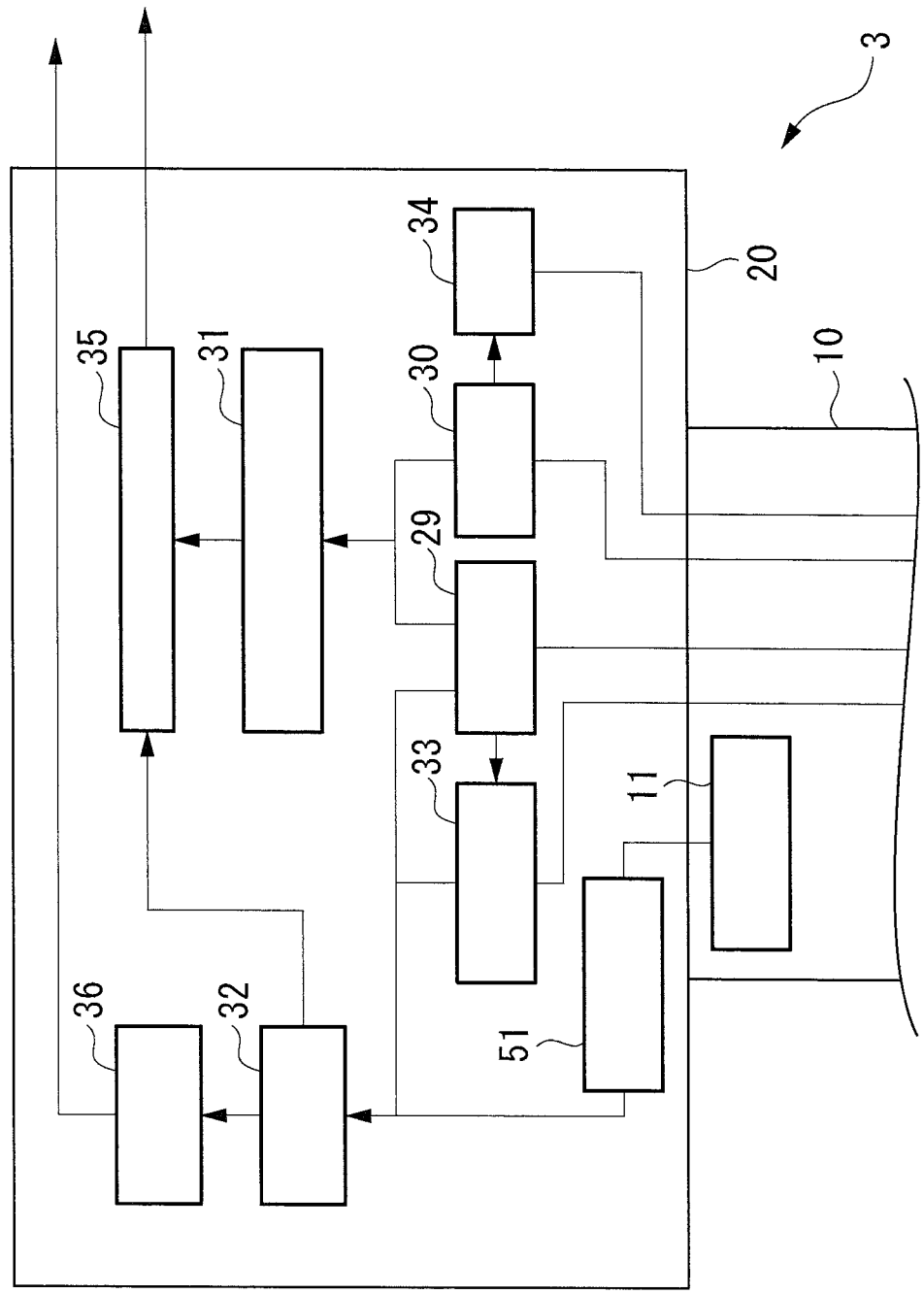
FIG. 11 is a functional block diagram of a fluoroscopy apparatus according to a third embodiment of the present invention.

As shown in FIG. 11, in the fluoroscopy apparatus 3 according to this embodiment, the image computing unit 20 is equipped with, as the functions thereof, the white-light-image generating section (return-light-image generating section) 29, the fluorescence-image generating section 30, the fluorescence-image correcting section 31, the error-image identifying section 32, the automatic exposure-time adjusting section 33, the automatic gain control (AGC) 34, the post-processing section (state determination section) 35, the error display section 36, and a scope-information reading section 51.

In addition to the components shown in FIG. 1, the endoscope 10 includes a scope-information holding section (storage section) 11.

An example of the scope-information holding section 11 is an IC chip in which an error identification condition for identifying an error region, peculiar to each of the scopes, is saved. Here, an example of the error identification condition is the gray level of a normalized white-light image.

The scope-information reading section 51 reads out the saved error identification condition of each scope from the scope-information holding section 11 and transmits the error identification condition of each scope to the error-image identifying section 32.

The error-image identifying section 32 identifies an error region on the basis of the error identification condition of each scope transmitted from the scope-information reading section 51. Specifically, the error-image identifying section 32 standardizes the white-light-image acquisition conditions by dividing the luminance values of the pixels of the white-light image generated by the white-light-image generating section 29 by the exposure time of the white-light color CCD 23 adjusted by the automatic exposure-time adjusting section 33. A region in which the gray levels of the normalized white-light image are higher than the gray level transmitted from the scope-information reading section 51 is identified as an error region.

The error identification condition serving as a reference for an error region differs from scope to scope. Thus, reading out the error identification condition from the scope-information holding section 11 by the error-image identifying section 32 via the scope-information reading section 51, as in the fluoroscopy apparatus 3 according to this embodiment, allows a suitable error identification condition to be set for each scope. This can improve the error-region identification accuracy.
Modification A modification of the fluoroscopy apparatus 3 according to this embodiment will be described hereinbelow.

Figure 12:
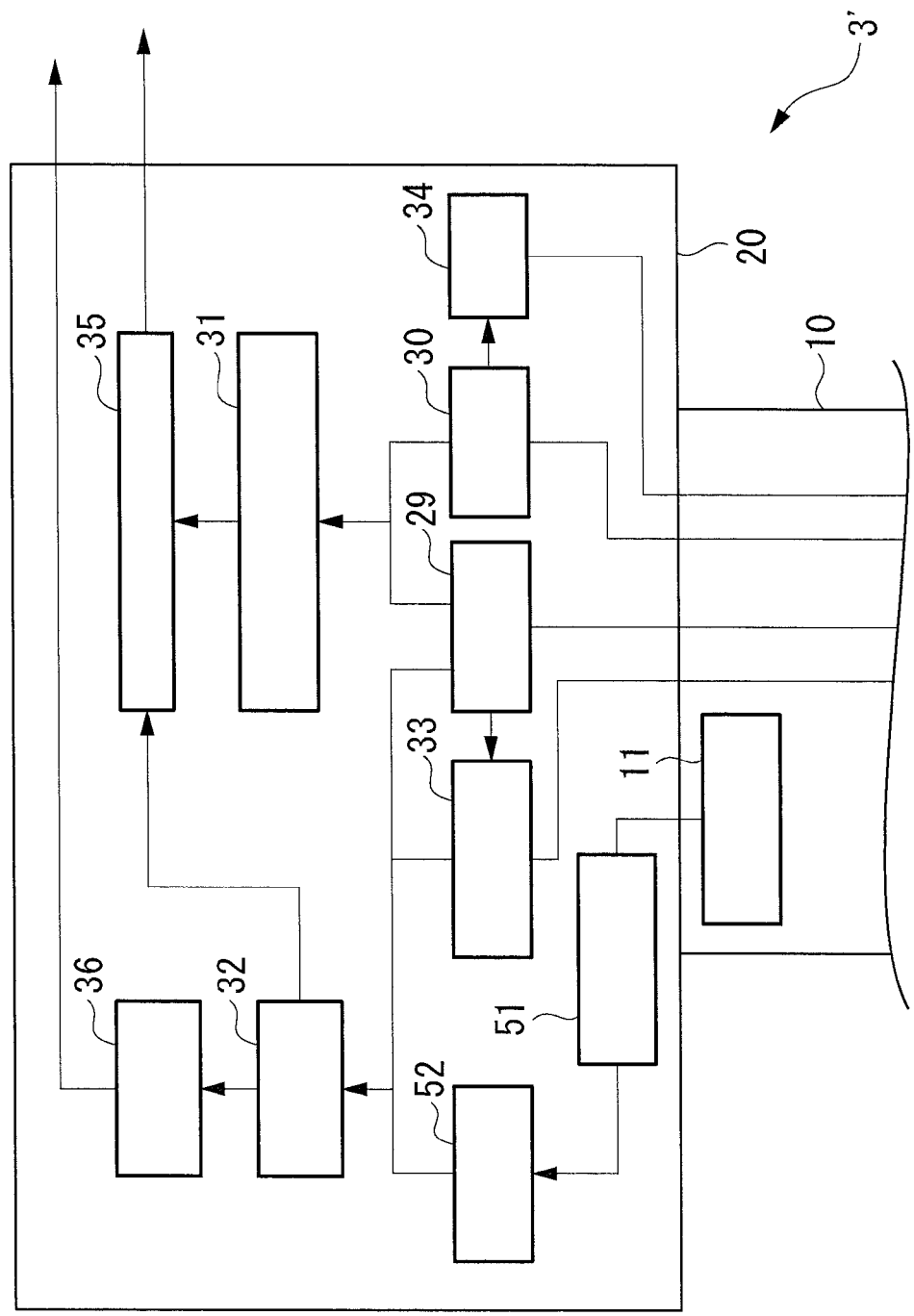
FIG. 12 is a functional block diagram of a fluoroscopy apparatus according to a modification of FIG. 11.

As shown in FIG. 12, in a fluoroscopy apparatus 3' according to this modification, the image computing unit 20 includes, as the functions thereof, the white-light-image generating section (return-light-image generating section) 29, the fluorescence-image generating section 30, the fluorescence-image correcting section 31, the error-image identifying section 32, the automatic exposure-time adjusting section 33, the automatic gain control (AGC) 34, the post-processing section (state determination section) 35, the error display section 36, the scope-information reading section 51, and an error-condition saving section (error-identification-condition storage section) 52.

The endoscope 10 includes the scope-information holding section (scope-information storage section) 11 in addition to the components shown in FIG. 1.

An example of the scope-information holding section 11 is an IC chip in which identification numbers unique to the individual scopes are stored.

The scope-information reading section 51 reads out the saved identification numbers unique to the individual scopes from the scope-information holding section 11 and transmits the scope information to the error-condition saving section 52.

The error-condition saving section 52 sets an error identification condition for identifying an error region on the basis of the scope information transmitted from the scope-information reading section 51. Specifically, the error-condition saving section 52 has a table in which the scope information and gray levels for identifying an error region in the normalized white-light image are associated with each other and sets the gray levels corresponding to the scope information transmitted from the scope-information reading section 51 as the error identification condition for identifying an error region. The error-condition saving section 52 transmits the thus-set error identification condition to the error-image identifying section 32.

With the fluoroscopy apparatus 3' according to this modification, by reading out the error identification condition stored in the error-condition saving section 52 and identifying an error region on the basis of the scope information stored in the scope-information holding section 11, a suitable error identification condition can be set for each scope and hence the error-region identification accuracy can be improved.
Fourth Embodiment Next, a fluoroscopy apparatus 4 according to a fourth embodiment of the present invention will be described with reference to the drawings. In the description of this embodiment, descriptions of commonalities with the fluoroscopy apparatus 1 according to the first embodiment will be omitted, and the difference will be mainly described.

The difference between the fluoroscopy apparatus 4 according to this embodiment and the fluoroscopy apparatus 1 according to the first embodiment is that the error identification condition for identifying an error region is automatically set.

Figure 13:
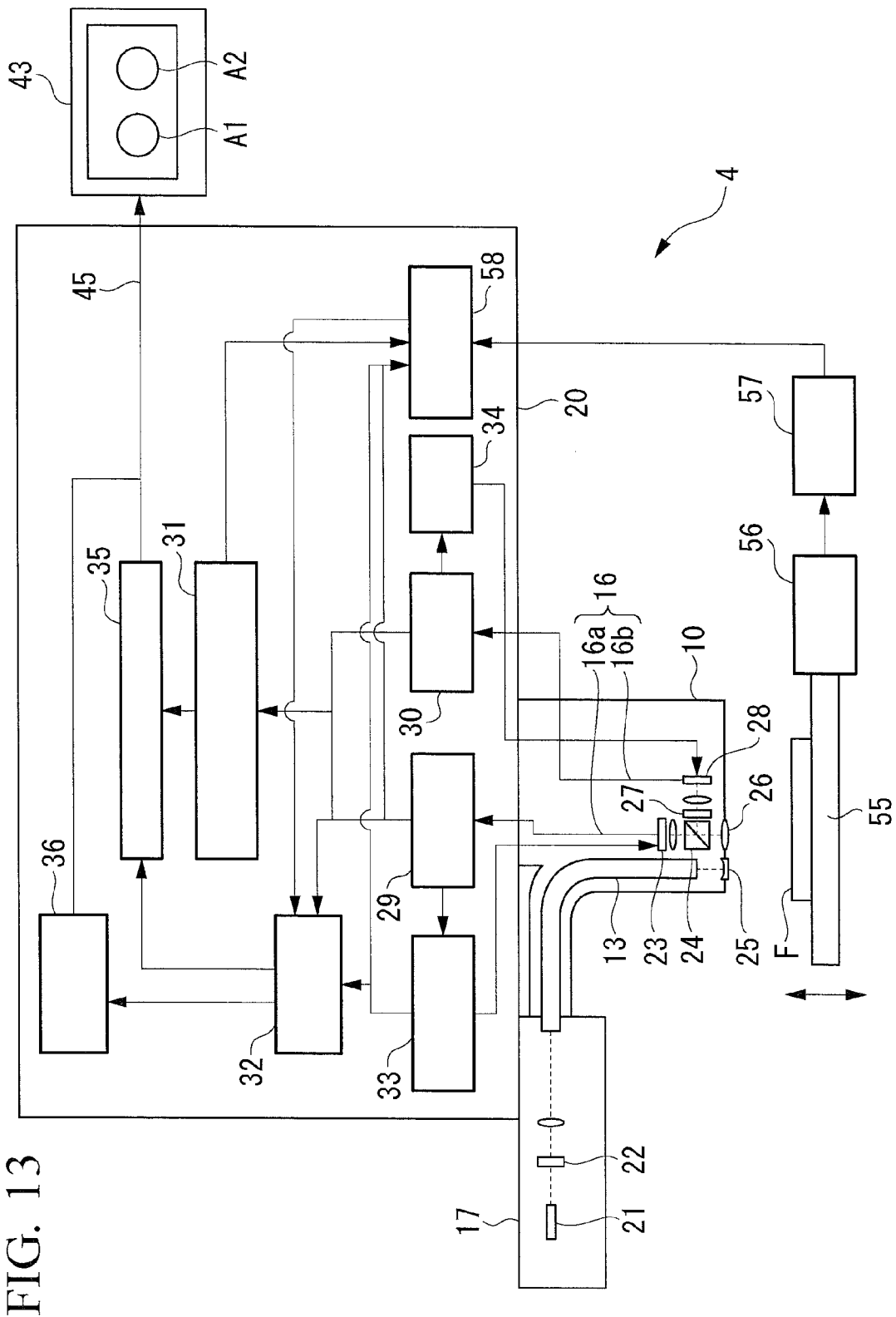
FIG. 13 is a functional block diagram of a fluoroscopy apparatus according to a fourth embodiment of the present invention.

As shown in FIG. 13, the fluoroscopy apparatus 4 according to this embodiment includes a stage 55 on which a standard sample F is to be placed, a distance moving section 56 that moves the stage 55 in a direction along the optical axis of the endoscope 10, and a distance-information receiving section 57 that detects the moving distance of the stage 55 caused by the distance moving section 56, in addition to the components shown in FIG. 1.

In the fluoroscopy apparatus 4 according to this embodiment, the image computing unit 20 includes, as the functions thereof, the white-light-image generating section (return-light-image generating section) 29, the fluorescence-image generating section 30, the fluorescence-image correcting section 31, the error-image identifying section 32, the automatic exposure-time adjusting section 33, the automatic gain control (AGC) 34, the post-processing section (state determination section) 35, the error display section 36, and an error-range determination section 58.

Figure 14:
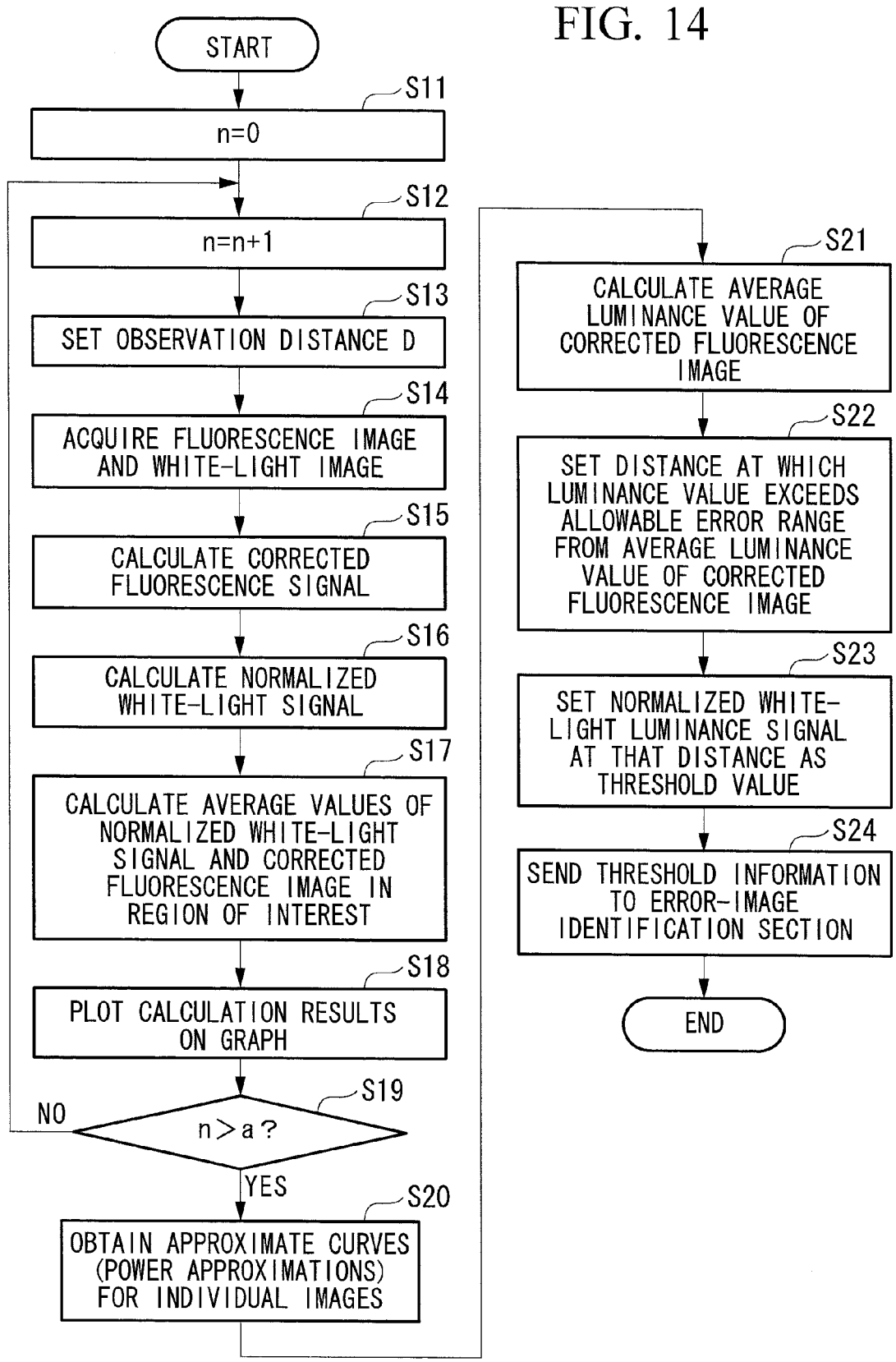
FIG. 14 is a flowchart explaining the process of the fluoroscopy apparatus in FIG. 13.

The operation of the fluoroscopy apparatus 4 having the above configuration will be described hereinbelow by using a flowchart shown in FIG. 14.

First, natural number n=0 is set (step S11).

Next, n=n+1 is set (step S12), and an observation distance D is set (step S13). In this case, the distance between the fluoroscopy apparatus 4 and the standard sample F is set at a fixed distance. From the second iteration onward, the distance is set to a distance other than the preceding observation distances.

Next, a white-light image generated by the white-light-image generating section 29 from the reflected light coming from the standard sample F is acquired, and a fluorescence image generated by the fluorescence-image generating section 30 from the fluorescence emitted from the standard sample F is acquired (step S14). Either of the white-light image and the fluorescence image may be generated first, or they may be generated at the same time.

Next, for the individual pixels, by dividing the luminance values of the fluorescence image by the luminance values of the white-light image using the fluorescence-image correcting section 31, a corrected fluorescence image is generated (step S15).

Next, the white-light-image acquisition conditions are standardized by dividing the luminance values of the pixels of the white-light image generated by the white-light-image generating section 29 by the exposure time of the white-light color CCD 23, adjusted by the automatic exposure-time adjusting section 33, with the error-image identifying section 32 (step S16).

Figure 15:
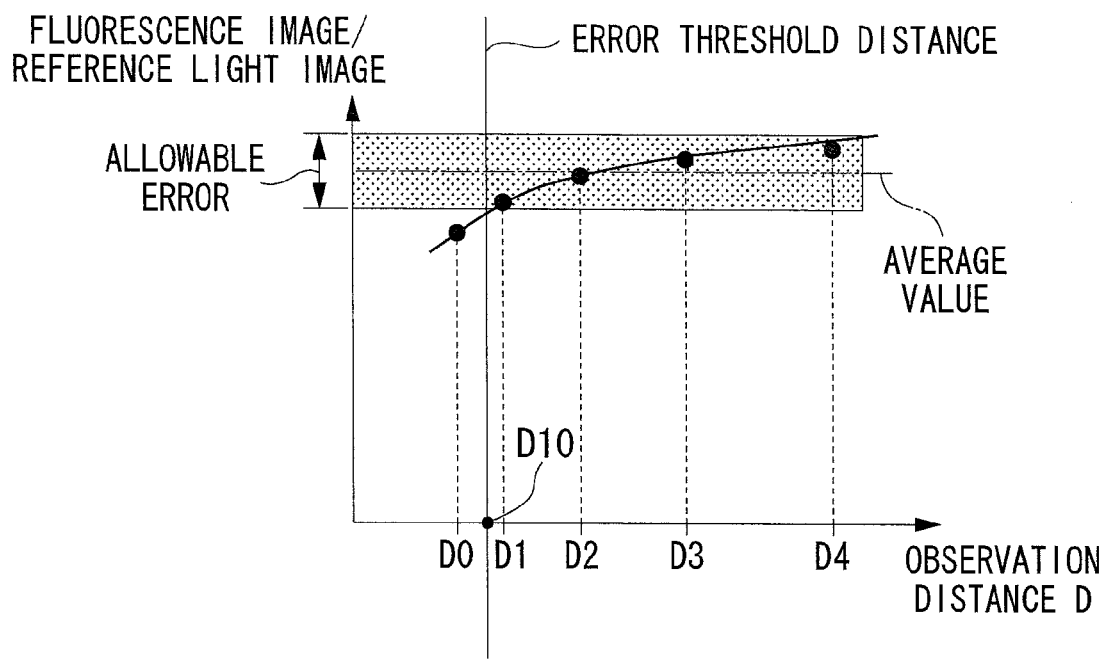
FIG. 15 is a graph showing the relationship between the luminance value of a corrected fluorescence image and the observation distance.
Figure 16:
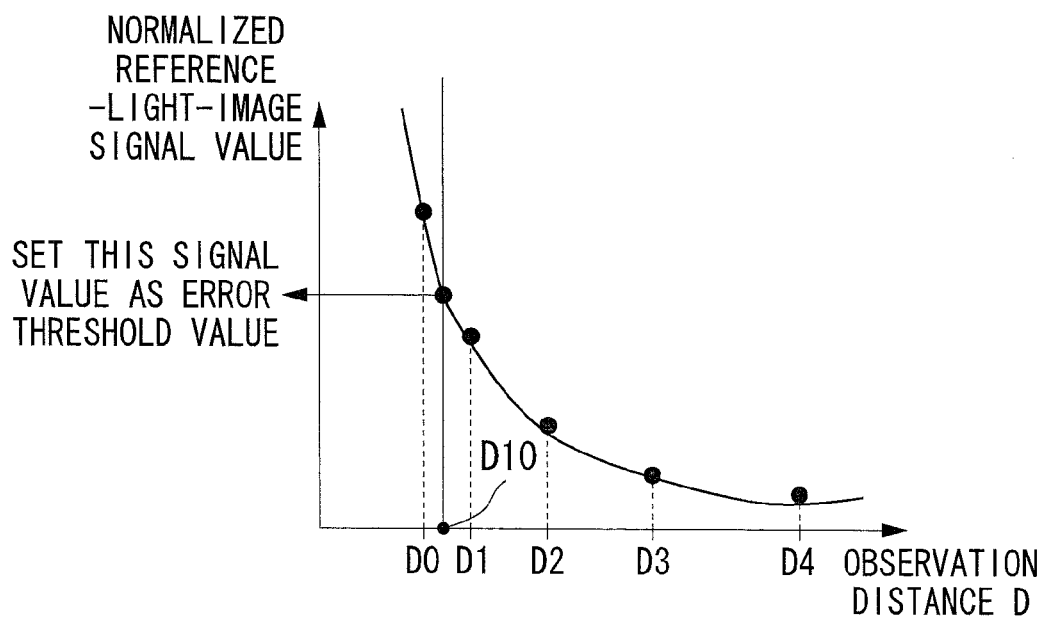
FIG. 16 is a graph showing the relationship between the signal value of a normalized white-light image and the observation distance.

Next, an average luminance value in a region of interest in the normalized white-light image and an average luminance value in the region of interest in the corrected fluorescence image are calculated (step S17), and the calculation results are plotted on graphs, as shown in FIGS. 15 and 16 (step S18). Here, FIG. 15 is a graph showing the relationship between the luminance value of the corrected fluorescence image and the observation distance D, and FIG. 16 is a graph showing the relationship between the signal value of the normalized white-light image and the observation distance D.

The processes from step S12 to step S18 are repeated a preset number of times a (step S19). Here, the symbol a denotes a preset integer larger than or equal to 2.

Next, approximate curves through the plot points are obtained for the corrected fluorescence image and the white-light image by a power approximation, as shown in FIGS. 15 and 16 (step S20).

Next, an average luminance value of the corrected fluorescence image is calculated (step S21).

Next, as shown in FIG. 15, an observation distance D10 at which the luminance value exceeds an allowable error range from the average luminance value of the corrected fluorescence image is set (step S22).

Next, as shown in FIG. 16, a signal value at which the observation distance is D10 in the normalized white-light image is set as an error threshold value (step S23).

The thus-set error threshold value is transmitted to the error-image identifying section 32 (step S24).

Thus, with the fluoroscopy apparatus 4 according to this embodiment, the stage 55 on which the standard sample F is placed can be moved by the distance moving section 56, and a threshold value for identifying an error region can be set from the relationship between the observation distance D and the luminance value of the corrected fluorescence image and the white-light image at that time. This allows a suitable error identification condition to be set, thus improving the error-region identification accuracy.

Although the individual embodiments of the present invention have been described in detail with reference to the drawings, the specific configurations are not limited to the embodiments, and design changes etc. that do not depart from the spirit of the present invention are also encompassed.

For instance, although an example in which the fluoroscopy apparatus according to the present invention is applied to an endoscope apparatus has been described in the embodiments, it may be applied to a microscope apparatus or the like.

Although an example in which white light is used as illumination light has been described in the embodiments, it is not limited to white light, and it may be reflected excitation light and so on.

Although the white-light-image generating section 29 has been described as applied to the case where it generates a white-light image from reflected light coming from the subject A, it may generate a return-light image from return light coming from the subject A, such as autofluorescence.

An example in which the automatic exposure-time adjusting section 33 is provided to adjust the luminance values of the pixels of the white-light image generated by the white-light-image generating section 29 has been described in the embodiments; instead, a light adjusting section that adjusts the amount of light emitted from the light source device 17 may be provided in the light source device 17. In this case, the error-image identifying section 32 may identify an error region using the gray level of a white-light image normalized using the intensity of illumination light emitted from the light source device 17.

REFERENCE SIGNS LIST 1, 2, 3, 3', 4 fluoroscopy apparatus
10 endoscope
11 scope-information holding section (scope-information storage section, storage section)
17 light source device (light source unit)
20 image computing unit
29 white-light-image generating section (return-light-image generating section)
30 fluorescence-image generating section
31 fluorescence-image correcting section
32 error-image identifying section
33 automatic exposure-time adjusting section
34 AGC (automatic gain control)
35 post-processing section (state determination section)
36 error display section
43 monitor (image display unit)
51 scope-information reading section
52 error-condition saving section (error-identification-condition storage section)
A subject

The invention claimed is:

1. A fluorescence-imaging apparatus comprising:
a light source configured to generate illumination light and excitation light to be radiated onto a subject; and
a processor comprising hardware, wherein the processor is configured to implement:
a fluorescence-image generating section configured to generate a fluorescence image by image-capturing fluorescence generated by the subject by irradiation with the excitation light from the light source;
a return-light-image generating section configured to generate a return-light image by image-capturing return light that returns from the subject by irradiation with the illumination light from the light source;
a fluorescence-image correcting section configured to generate a corrected fluorescence image in which luminance values of pixels are normalized by dividing the luminance values of the pixels of the fluorescence image generated by the fluorescence-image generating section by the luminance values of the pixels of the return-light image generated by the return-light-image generating section; and
an error-image identifying section configured to:
standardize image-acquisition conditions for the return-light image generated by the return-light-image generating section;
identify an error region, which is a region in which the luminance values of the corrected fluorescence image exceed a preset allowable error range, on the basis of a gray level of the normalized return-light image; and
control a display to display the error region.

2. The fluorescence-imaging apparatus according to claim 1, wherein the error-image identifying section implemented by the processor is configured to identify the error region by using an area of a region having a high gray level in the normalized return-light image.

3. The fluorescence-imaging apparatus according to claim 1, wherein the error-image identifying section implemented by the processor is configured to control the display to display the return-light image generated by the return-light-image generating section and the error region so as to be superimposed on the return-light image generated by the return-light-image generating section.

4. The fluorescence-imaging apparatus according to claim 3, wherein the error-image identifying section implemented by the processor is configured to control the display to display the error region in a color different from that around the error region.

5. The fluorescence-imaging apparatus according to claim 1, wherein if the error region is identified by the error-image identifying section, the error-image identifying section controls the display to display an error indication on a screen.

6. The fluorescence-imaging apparatus according to claim 1, wherein the error-image identifying section implemented by the processor is configured to identify the error region on the basis of a gray level of a peripheral region in the normalized return-light image.

7. The fluorescence-imaging apparatus according to claim 1, wherein the error-image identifying section implemented by the processor is configured to identify the error region on the basis of gray levels of a peripheral region and a central region in the normalized return-light image.

8. The fluorescence-imaging apparatus according to claim 1, wherein the error-image identifying section implemented by the processor is configured to identify the error region on the basis of a gray level of a region corresponding to a vicinity of an emitting end of the illumination light in the normalized return-light image.

9. The fluorescence-imaging apparatus according to claim 1, further comprising:
an elongated scope; and
an error-identification-condition storage provided in the elongated scope, wherein the error-identification-condition storage is configured to store an error identification condition serving as a reference for the error region,
wherein the error-image identifying section implemented by the processor is configured to:
read out the error identification condition from the error-identification-condition storage; and
identify the error region based on the error identification condition read out from the error-identification-condition storage.

10. The fluoroscopy apparatus according to claim 1, further comprising:
an elongated scope;
a scope-information storage provided in the elongated scope, wherein the scope-information storage is configured to store information about the elongated scope; and
an error-identification-condition storage configured to store a plurality of error identification conditions serving as a reference for the error region,
wherein the error-image identifying section implemented by the processor is configured to:
read out the error identification conditions stored in the error-identification-condition storage based on the information stored in the scope-information storage; and
identify the error region based on the error identification conditions read out from the error-identification-condition storage.

* * * * *